United States Patent

Danna et al.

[11] Patent Number: 5,633,675
[45] Date of Patent: May 27, 1997

[54] SHADOW PROBE

[75] Inventors: Dominick Danna, Syracuse; Raymond A. Lia, Auburn, both of N.Y.

[73] Assignee: Welch Allyn, Inc,, Skaneateles Falls, N.Y.

[21] Appl. No.: 370,866

[22] Filed: Jan. 10, 1995

Related U.S. Application Data

[63] Continuation-in-part of Ser. No. 17,603, Feb. 16, 1993, abandoned.

[51] Int. Cl.[6] .................... H04N 7/18; A62B 1/04
[52] U.S. Cl. .................... 348/65; 348/68; 348/85; 600/109; 600/129
[58] Field of Search .................... 348/65, 66, 67, 348/68, 72, 75, 76, 82, 84; 600/109, 112, 129, 130, 160, 171, 176, 181

[56] References Cited

U.S. PATENT DOCUMENTS

| | | |
|---|---|---|
| 2,932,294 | 4/1960 | Fourestier . |
| 4,281,931 | 8/1981 | Chikama . |
| 4,576,147 | 3/1986 | Hashiguchi . |
| 4,588,294 | 5/1986 | Siegmund . |
| 4,732,474 | 3/1988 | Chikama . |
| 4,867,138 | 9/1989 | Kubota et al. . |
| 4,980,763 | 12/1990 | Lia . |
| 4,995,396 | 2/1991 | Inaba et al. .................... 348/65 |
| 5,051,824 | 9/1991 | Nishigaki . |

FOREIGN PATENT DOCUMENTS

| | | |
|---|---|---|
| 3629435 | 3/1987 | Germany . |
| 9016829 | 4/1991 | Germany . |

OTHER PUBLICATIONS

Patent Abstracts of Japan, vol. 16, No. 85 (P-1319), 28 Feb. 1992 & JP-A-03 269407 (Olympus Optical Co. Ltd.), 2 Dec. 1981.

*Primary Examiner*—Amelia Au
*Attorney, Agent, or Firm*—Harris Beach & Wilcox, LLP

[57] ABSTRACT

A device for measuring the size of targets viewed with a borescope having a housing with a longitudinal axis and a distal viewing end with an optically transparent window set therein, a source of target illumination which projects a cone of illumination so that the axis of the cone of illumination is at an angle of less than 90° with the housing axis, a contrasting shadow generated in association with the illumination source so as to project the contrasting shadow on the target, an image detector disposed adjacent to the source of illumination, directed so as to detect the image of the target and the contrasting shadow, a display for viewing the target and shadow as detected by the image detector, and a measuring device for measuring the parameters of the contrasting images on the display so that the actual size of the target can be determined.

4 Claims, 2 Drawing Sheets

SHADOW PROBE

This is a continuation-in-part of application Ser. No. 08/017,603 filed Feb. 16, 1993 now abandoned.

BACKGROUND OF THE INVENTION

This invention relates generally to a borescope or endoscope for providing a full color video image of an inaccessible area, and more particularly to an improved system for measuring the size of an object viewed by the imager head of the device for display on the video image display of the borescope or endoscope (hereinafter termed, collectively, "borescope").

The prior art shows a number of devices for providing a full color video picture of a remotely situated target, such as the inside of a jet engine or a human ulcer. Such devices have become increasingly sophisticated over time; they now include a video screen, an external light source, and an elongated flexible insertion tube. Video processing functions are usually handled outside the insertion tube. The insertion tube contains, through much of its length, fiber optic bundles for transmitting light from the external source to the imager head at distal end of the tube. This imager head comprises a solid state sensor and lens system set in a housing having a transparent window, usually at the tip, for viewing the target. The information from the solid state sensor is relayed to the external video display into which the proximal end of the insertion tube is connected or plugged.

When viewing a target through a borescope, there is often no reference standard which can be used to determine the size of the target, the observed size being a function not only of the target's size, but also of its distance from the imager head. U.S. Pat. No. 4,980,763 to Lia and owned by a common assignee of the present applicants, teaches a method for determining the size of a target viewed through a borescope. The method involves generating a shadow of a known shape in association with the illumination that is cast upon the target. The shadow appears in the plane of the target and both the target and the shadow are detected by the imager head. Because the location of the shadow generating image is known, the magnification of the image is also known, and therefore computation of the actual size of the target can be made. This information is relayed to the video screen display.

The borescope used in the earlier invention of Lia operates well to provide desired target information. However, because the illumination and shadow producing components lie on a parallel axis to that of the image detection system, the distal end of the insertion tube must be of sufficient diameter to accommodate these components while providing an area of the optically transparent tip large enough to allow substantial overlap of the areas of illumination and detection. In essence, the minimal diameter of this borescope is determined by the sum of the maximum width of the image detection system and the diameter of the cross section of the cone of light created by the illumination source in the plane of the optically transparent window at the tip of the borescope.

The U.S. Pat. No. 4,867,138 to Kubota et al. teaches a method wherein the outside diameter of the base side of a rigid electronic endoscope is made smaller than the tip part. The method involves the use of a prism to direct the image detection means at an angle of less than 90° to the longitudinal axis of the housing of the endoscope. This method operates well to reduce the diameter of the base side of the rigid endoscope allowing a treating tool and irrigating liquid to be fed and drained. However, it does not reduce the diameter of the imager head because the image detection means is placed perpendicular to the longitudinal axis.

There are applications which require an insertion tube of smaller diameter than is possible using this configuration. A number of patents have been directed toward achieving a high degree of compactness. See, for an example U.S. Pat. No. 4,491,865 to Danna et al, owned by a common assignee of the present applicants. Thus, it is desirable to implement the shadow technique of Lia so that size measurements can be obtained, while creating a more compact insertion tube end than is shown in that disclosure.

SUMMARY OF THE INVENTION

It is therefore a primary object of the present invention to provide a more compact target inspecting and measuring system used in borescopes.

It is another object of the present invention to provide a more compact target inspecting and measuring system for measuring the size of a target as well as its appearance from a borescope imager head.

It is still another object of the present invention to provide a more compact target inspecting and measuring system for measuring the size of a target as well as its appearance from a borescope imager head, in which the optically transparent tip of the imager head is elliptically shaped.

It is yet another object of the present invention to provide a more compact target inspecting and measuring system for measuring the size of a target as well as its appearance from a borescope imager head in which the fiber optic bundle is immediately adjacent the charged coupled device (CCD) imager.

These and other objects of the present invention are attained by a device for measuring the size of targets viewed with a borescope comprising: a housing with a longitudinal axis and a distal viewing end with an optically transparent illumination window and an optically transparent optic window set adjacently therein; a source of target illumination which projects a cone of illumination through the illumination window so that the axis of the cone of illumination is at an angle of less than 90° with the housing axis; a contrasting shadow generated in association with the illumination source so as to project the contrasting shadow on or in the plane of the target; an image detector disposed adjacent to the source of illumination and behind the optic window, directed so as to detect the image of the target and the contrasting shadow; a display for viewing the target and shadow as detected by the image detector; and a measuring device for measuring the parameters of the contrasting images on the display so that the actual size of the target can be determined.

BRIEF DESCRIPTION OF THE DRAWINGS

For a better understanding of these and other objects of the present invention, reference is made to the detailed description of the invention which is to be read in conjunction with the following drawings, wherein.

DETAILED DESCRIPTION OF THE INVENTION

Figure 3:
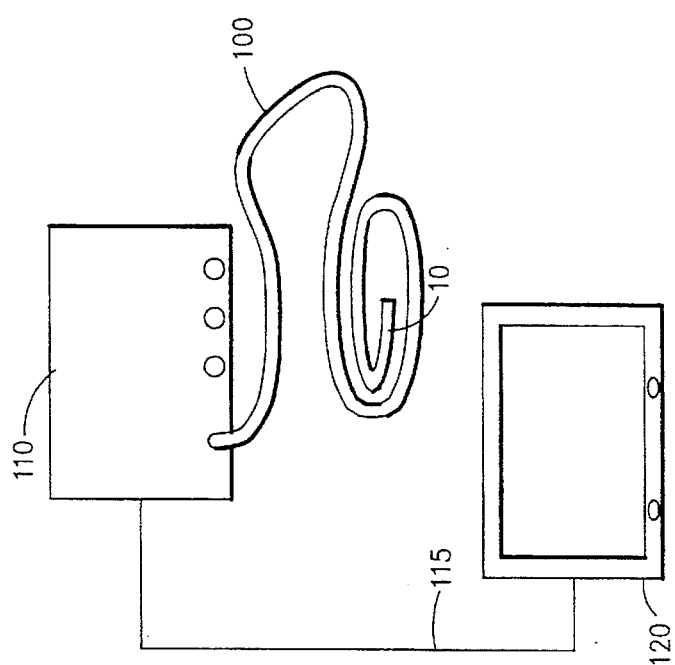
FIG. 3 is a block diagram schematic of the present invention.

Referring, now to FIG. 3 there is shown a general schematic of the preferred embodiment of a borescope such as is seen in this invention. A general control box 110 containing a light source, external control mechanisms for use by the person handling the borescope, and internal control circuitry which is linked by electrical connection 115 to a monitor 120. The general control box also is linked to the borescope insertion tube 100 which ends in a borescope imager head 10. Other configurations are possible, such as a having a separate borescope handle containing some or all of the external and/or internal controls.

Figure 4:
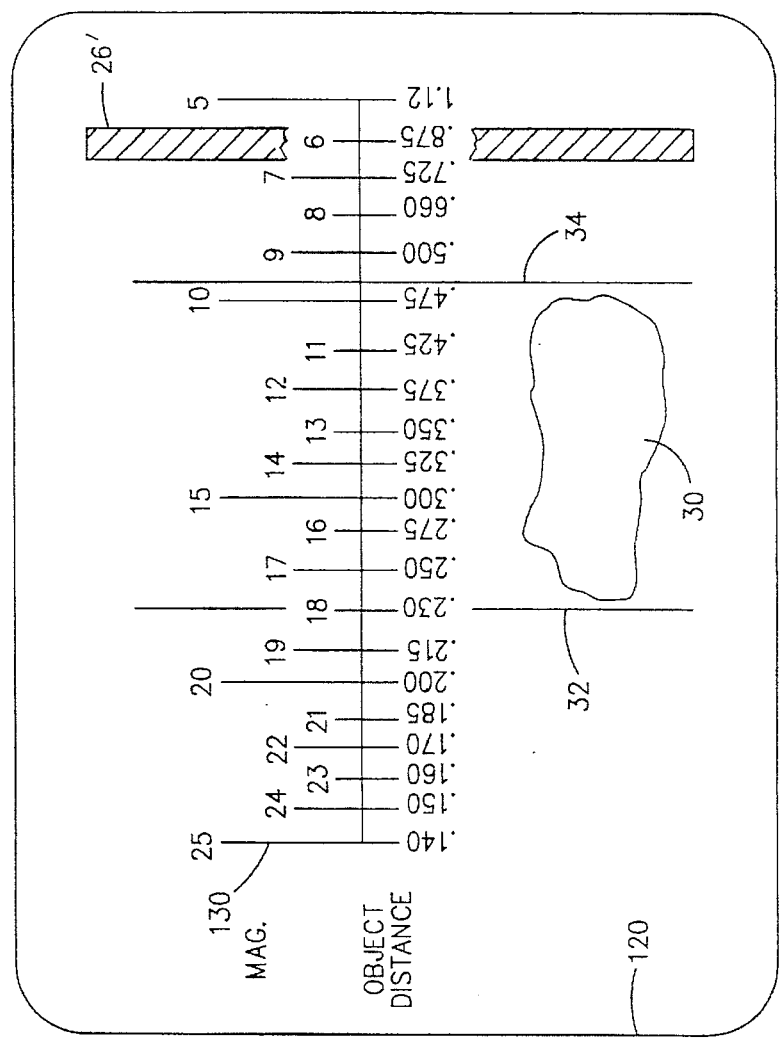
FIG. 4 is an elevation of a display screen with a display of target to be measured showing electronic cursors for measurement.

FIG. 4 shows one possible form of screen display on the monitor 120 as depicted in prior U.S. Pat. No. 4,980,763. In this embodiment the size of the target object is adjusted via calculations using its measured size in proportion to the position of the shadow in the image. The size-adjusted image is then displayed on the screen which also may contain an on screen scale indicator or gauge 130.

Figure 2:
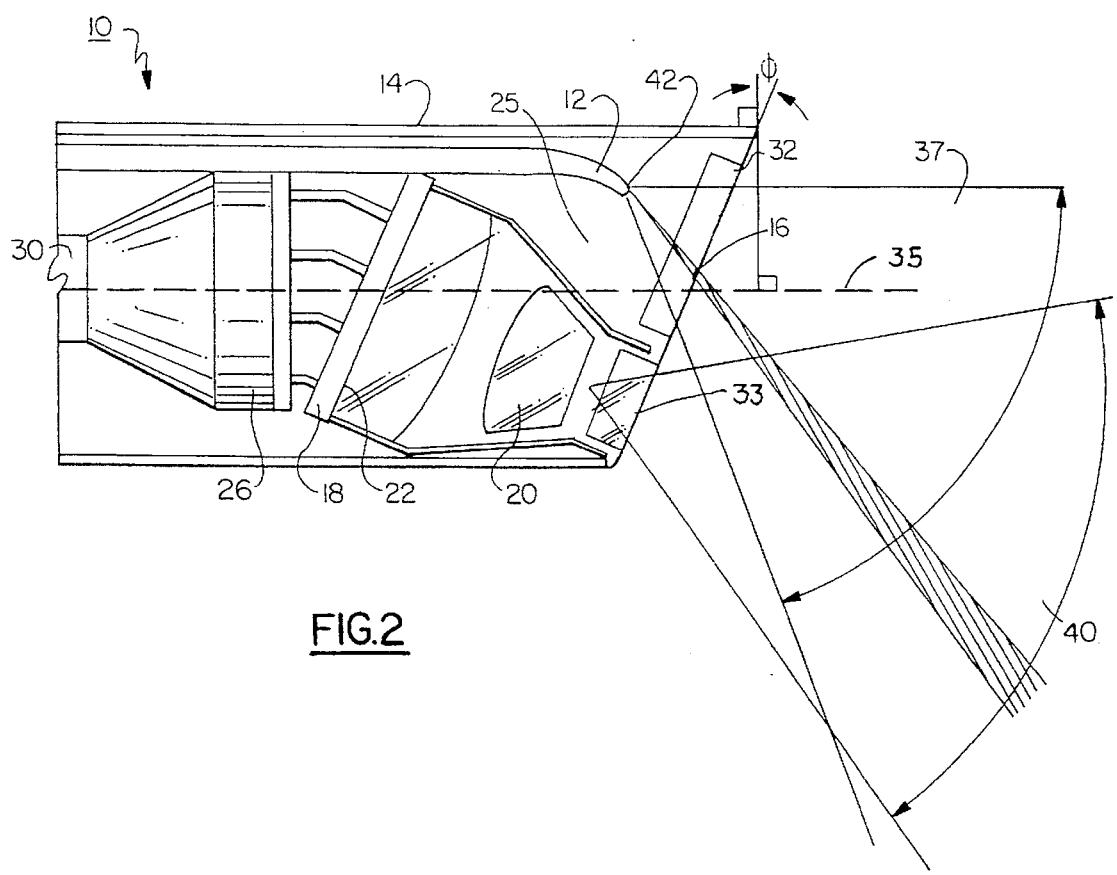
FIG. 2 is a partial sectional view of the imager head of a borescope according to the present invention.

Referring now to FIG. 2, there is shown a borescope imager head 10 housed in a small diameter housing 14. The borescope imager head 10 has a fiber optic bundle 12 for conveying light from an illumination source outside the head, and a video image sensor 18 with associated optics 20 placed distally at least a given distance from the image sensor. The light from the tip 42 of the fiber optic bundle 12 passes through an optically transparent illumination window 32 into which is set, etched, drawn or otherwise affixed an opaque object 16 that can cast a shadow either on the target or in the plane of the target. As known in the art, the video image sensor 18 comprises a CCD imager 22, a hybrid circuit 26 connected thereto by well known means such as wires, and a cable 30 for relaying the video image detected through an optically transparent optic window 33 to a monitor or other device.

Figure 1:
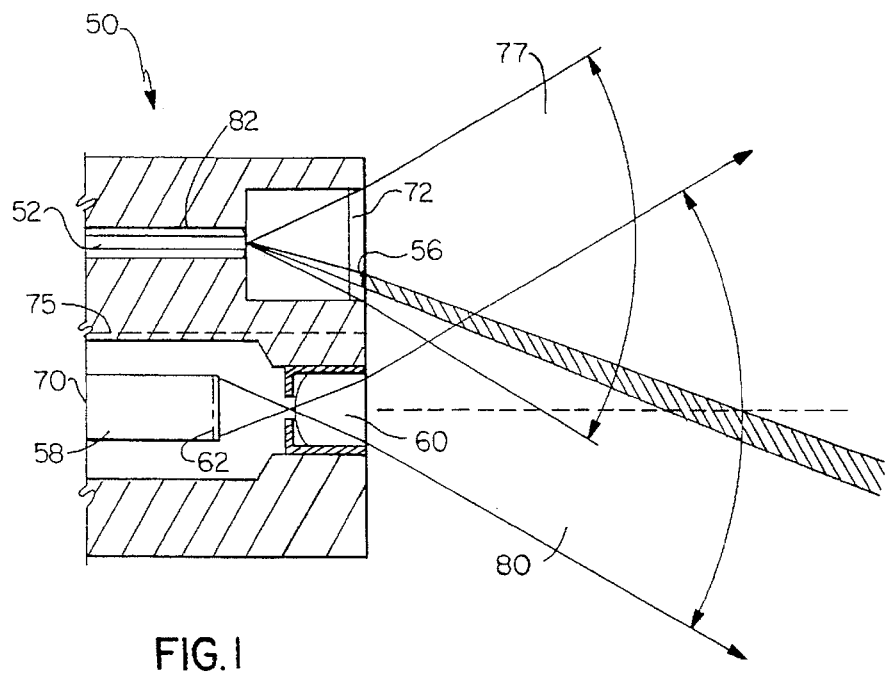
FIG. 1 is a partial sectional view of the imager head of a borescope of the prior art.

In the prior art, as can be seen in FIG. 1, the same basic elements also existed, that is a borescope imager head 50 having a fiber optic bundle 52 for conveying light from an illumination source, an object 56 capable of casting a shadow, and a video image sensor 58 with associated optics 60 and a cable 70 for relaying the video image to a monitor or other device.

This device of the prior art, however, while very compact, was limited in its compactness by both the size and geometry of the components and the geometry of their relationship. Light projects from a source in a cone shaped field. Likewise the optical field of view of an image sensor extends as a cone shaped field from the sensor. In the prior art the optically transparent window 72 of the borescope imager head 50 was cut perpendicular to the longitudinal axis 75 of the borescope imager head 50, presenting a circular surface. The axes of both the cone of illumination 77 and the cone of detection 80 were parallel to that of the borescope imager head. The CCD imager 62 was located in a plane perpendicular to that of these axes. In addition, the distal end 82 of the fiber optic bundle 52 was set sufficiently distant from the optically transparent window 72 so that the cone of illumination 77 overlapped the cone of detection 80, in order that a target (not shown) may be illuminated and detected. The shadow casting image 56 was within the cone of illumination and thus its shadow was, of necessity, in the target region. Using this configuration, the diameter of the borescope imager head 50 had to be at least the sum of the diameter of the CCD imager 62 and the diameter of the cone of illumination 77 at the plane of the optically transparent window 72.

In the instant invention, however, the optically transparent illumination window 32 (IW) is set at an angle of less than 90° a plane perpendicular to to the longitudinal axis 35 of the borescope imager head 10, presenting an elliptical surface (not shown). The angle $\theta$ at which the window is set is between 15° and 45°, with an angle $\theta$ of 20° being preferred. The axes of both the cone of illumination 37 and the cone of detection 40 are also set at an angle of less than 90° to the axis of the borescope housing 14, again between 15° and 45°, with an angle of 20° being preferred. This is accomplished by placing the image recording face of the CCD imager 22 at an angle of less than 90° a plane perpendicular to to the axis of the housing, while leaving the face of the hybrid circuit 26 that connects to the CCD imager 22 perpendicular to the housing axis. This angle may be between 15° and 45°, with 20° being preferable. This creates an area 25 that allows for the bending of the fiber optic bundle 12. This results in tilting of the optic and imager assembly. The angle of tilt is the same with respect to the housing axis as is that of the windows. Thus, the CCD imager 22 is located in a plane at an angle of less than 90° to a plane perpendicular to the longitudinal axis 35 of the borescope imager head 10. The distal end 42 of the fiber optic bundle 12 is still set sufficiently far from the optically transparent illumination window 32 so that the cone of illumination 37 completely overlaps the cone of detection 40 within the viewing range of the optics, in order that a target (not shown) may be illuminated and detected. Again, since the shadow casting image 16 is within the cone of illumination, its shadow is also, of necessity, in the target region. Due to this configuration, the diameter of the imager head 10 (D) is equal to the cosine of the angle $\theta$ times the sum of the diameter of the illumination window 32 (IW) plus the diameter of the optic window 33 (OW) plus twice the thickness (t) of housing wall 14.

Not shown, and common to both this and the prior art, is a video monitor or other display device on which the images of both the target and the shadow can be shown. Also not shown, and common to both this and the prior art is hardware, firmware or software which takes as input the information concerning measurement parameters of the target and shadow obtained from the CCD imager and uses this information to determine the actual size of the target. The information as to actual size thus determined can be used to appropriately adjust the size of the target as shown on the display device to correct for the distance of the target from the probe. Alternatively, the information can be relayed to the user by other means, such as a numeric display, on-screen scale indicators or the like.

It should be noted that while, in the preferred embodiment, the light path both from the light source to the target and from the target to the detector is linear, this is not necessary. The direction of either or both of these light paths may be controlled by intermediary devices, such as prisms or mirrors. In this case the light sources and/or detecting means respectively need not be set at an angle to the axis of the housing as described above. All that is necessary is that the light source and detecting means be adjacent one another and that the path of light immediately prior to reaching the target and immediately upon leaving the target be at an angle of less than 90° with respect to the axis of the borescope housing.

While this invention has been explained with reference to the structure disclosed herein, it is not confined to the details set forth and this application is intended to cover any modifications and changes as may come within the scope of the following claims:

What is claimed is:

1. A borescope having a compact imager head comprising:

an elongated cylindrical housing having a given wall thickness, a diameter (D), and a longitudinal axis;

said housing having a circular end face at its distal end that forms an angle $\theta$ with a plane perpendicular to said longitudinal axis, said angle being less than 90°;

an illumination window and an optic window mounted adjacent each other along a diameter of the end face;

an imager having a flat recording surface, said imager being mounted behind the optic window to view a target image outside of said housing, said recording surface being parallel with said end face, said imager being positioned a predetermined distance behind the optic window to establish a region behind the illumination window of a shape and size to accommodate the distal end of a light carrying fiber bundle for illuminating a target within the viewing range of the imager without interfering with the target image;

shadow generating means associated with said light carrying fiber bundle to produce a contrasting shadow in a target plane;

display means connected to said imager for viewing and measuring the target image and a shadow image in the target plane; and measuring means for measuring parameters of the target image and the shadow image on said display so that the attached size of the target can be determined, wherein the diameter (D) of the imager head is substantially expressed by the relationship $D = \cos\theta(OW + IW + 2t)$;

where:

OW = the length of the optic window along the diameter of the end face;

IW = the length of the illumination window along the diameter of the end face; and 2t = twice the wall thickness.

2. The borescope of claim 1 wherein the angle $\theta$ is between 15° and 45°.

3. The borescope of claim 1 wherein the angle $\theta$ is about 20°.

4. The borescope of claim 1 wherein said parameter measurements are used to adjust the target image on the display means in proportion to its distance from the imager.

* * * * *